United States Patent
Ledermann et al.

(10) Patent No.: US 10,533,980 B2
(45) Date of Patent: Jan. 14, 2020

(54) METHOD FOR CORRECTING MEASURED VALUES OF A SENSOR ELEMENT

(75) Inventors: Bernhard Ledermann, Weil der Stadt (DE); Ulrich Belzner, Schwieberdingen (DE); Thomas Steinert, Weinstadt (DE)

(73) Assignee: Robert Bosch GmbH, Stuttgart (DE)

( * ) Notice: Subject to any disclaimer, the term of this patent is extended or adjusted under 35 U.S.C. 154(b) by 1022 days.

(21) Appl. No.: 14/350,963

(22) PCT Filed: Sep. 13, 2012

(86) PCT No.: PCT/EP2012/067963
§ 371 (c)(1),
(2), (4) Date: Aug. 29, 2014

(87) PCT Pub. No.: WO2013/068157
PCT Pub. Date: May 16, 2013

(65) Prior Publication Data
US 2015/0027196 A1    Jan. 29, 2015

(30) Foreign Application Priority Data
Nov. 11, 2011    (DE) .......... 10 2011 086 144

(51) Int. Cl.
*G01N 33/00*    (2006.01)
*F01N 11/00*    (2006.01)

(52) U.S. Cl.
CPC ........ *G01N 33/0006* (2013.01); *F01N 11/007* (2013.01)

(58) Field of Classification Search
CPC ...... F23N 5/006; F23N 5/003; F23N 2035/06; F23N 5/02; F23N 5/082; F23N 5/08;
(Continued)

(56) References Cited

U.S. PATENT DOCUMENTS

| 5,137,615 A | * | 8/1992 | Friese | ............. G01N 27/4071 204/410 |
| 5,554,269 A | | 9/1996 | Joseph et al. | |

(Continued)

FOREIGN PATENT DOCUMENTS

| CN | 101193585 A | 6/2008 |
| CN | 101223417 A | 7/2008 |

(Continued)

OTHER PUBLICATIONS

International Search Report, PCT International Application No. PCT/EP2012/067963, dated Jan. 2, 2013.

*Primary Examiner* — John Fitzgerald
*Assistant Examiner* — Truong D Phan
(74) *Attorney, Agent, or Firm* — Norton Rose Fulbright US LLP; Gerard Messina

(57) ABSTRACT

A measured value of a sensor element is obtained during repeatedly executed measuring periods for performing different measurements and for setting different operating states, the sensor element being electrically connected in a periodically alternating manner, in consecutive switching positions, in a predefined order, where at least one measurement for determining the measured value is performed repeatedly within a measuring period for determining individual values at predefined switching positions, the measured value being determined from the individual values. Using the switching position within the measuring period, the operating state of the sensor element preceding the individual measurement, and therefore, the influence of the preceding circuit configuration on the individual measured value, is known, and the individual values are correspondingly corrected. By correcting the individual values, the measured value determined from the individual values is also corrected.

7 Claims, 2 Drawing Sheets

(58) Field of Classification Search
CPC ...... F23N 2027/36; F23Q 9/04; F23D 14/725;
G01N 33/0006; G01N 27/4065; G01N
33/007; G01N 27/419; G01N 27/4175;
G01N 27/4163; G01N 27/407; G01N
27/4077; F01N 11/007; F02D 41/1456;
F02D 41/1494; G01P 21/00; G01D 3/022;
G01D 3/08; G01D 18/00; G01M 15/102
USPC ................. 73/1.01, 1.02, 23.31, 23.32, 1.06;
431/76, 77, 79; 60/276; 123/688
See application file for complete search history.

(56) References Cited

U.S. PATENT DOCUMENTS

| | | | |
|---|---|---|---|
| 6,301,951 B1 | 10/2001 | Lenfers et al. | |
| 2003/0024296 A1 | 2/2003 | Radu et al. | |
| 2012/0050180 A1* | 3/2012 | King | G06F 3/0416 |
| | | | 345/173 |
| 2013/0163003 A1* | 6/2013 | Massow | G01B 9/02004 |
| | | | 356/479 |
| 2014/0311237 A1* | 10/2014 | Wagner | G01F 1/6965 |
| | | | 73/204.18 |

FOREIGN PATENT DOCUMENTS

| | | |
|---|---|---|
| CN | 102016557 A | 4/2011 |
| DE | 198 38 466 A1 | 3/2000 |
| DE | 101 63 912 A1 | 2/2003 |
| DE | 10 2006 061 565 A1 | 7/2008 |
| DE | 10 2008 001 697 A1 | 11/2009 |
| DE | 102008001697 * | 11/2009 |
| JP | 59142449 A | 8/1984 |
| JP | 2001221095 A | 8/2001 |
| JP | 2001242126 A | 9/2001 |
| JP | 2007271332 A | 10/2007 |
| JP | 2010236358 A | 10/2010 |
| JP | 2011520112 A | 7/2011 |
| WO | 02082067 A | 10/2002 |

* cited by examiner

METHOD FOR CORRECTING MEASURED VALUES OF A SENSOR ELEMENT

FIELD OF THE INVENTION

The present invention relates to a method for correcting a measured value of a sensor element, wherein the measured value is obtained during repeatedly executed measuring periods for performing different measurements and for setting different operating states. The sensor element is electrically connected by a circuit arrangement in a periodically alternating manner, in consecutive switching positions, in a predefined order. At least one measurement for determining the measured value is performed repeatedly within a measuring period, at predefined switching positions, and in this manner, individual measured values are determined at the predefined switching positions, and the measured value is determined from the individual measured values.

BACKGROUND

In general, sensor elements are electrically connected by an external measuring system. In this context, it is often provided that the measuring system switches over between different measurements and operating states of the sensor element, using different circuit states. The switching-over may take place periodically in a predefined order, so that a circuit state is always set at the same switching position or positions of a measuring period.

Sensor elements, on which such cyclically alternating, protective circuits are provided, include, for example, wide-range lambda probes, as are used for monitoring the composition of the exhaust gas of internal combustion engines for maintenance of limiting values. The correct functioning of such exhaust-gas sensors and, in particular, their resistance to aging, as well, are a strong function of their protective electronic circuit. The functional blocks of such a protective circuit are described, for example, in the document DE 10 2006 061 565 A1.

In the document DE 10 2008 001697 A1, an improved wiring configuration is described, which allows, in addition to the operation of the exhaust-gas sensor, information about the operating state of the wide-range lambda probe used there as an exhaust-gas sensor to be acquired, to be stored, and to be retransmitted to a superordinate engine control unit via a digital interface. This set-up allows a diagnosis of the lead-wire connections between the protective circuit and the wide-range lambda probe, for a short circuit and a break, as well as for maintenance of permissible voltages at the terminals. The operation readiness of the exhaust-gas analyzer probe may be detected, and its electrode polarization and the aging may be continuously monitored. In order to perform these measurements and to set the different operating states, the wide-range lambda probe is variably connected electrically in successive circuit states of the control electronics, and accordingly acted upon electrically in a variable manner. In this context, previous circuit states may influence measurements. For example, a circuit state may produce unwanted polarization of a Nernst cell of the wide-range lambda probe, which, in a subsequent circuit state, may lead to falsification of the measured value of the Nernst voltage at the Nernst cell. If the circuit states are selected periodically, then the influence on the measured values is also periodic. Today, such measuring errors are mostly corrected using a low-pass filter, through which, however, the signal dynamics are reduced.

SUMMARY

In the ideal case, the successive measurements and operating states do not influence one another. In practice, however, a measurement may be falsified by an operating state previously set, e.g., as a result of a polarization effect in the sensor element. Consequently, the falsification of the measurement is a function of the operating state set previously, and therefore, a function of the switching position at which the measurement is performed within the measuring period.

An object of the present invention is to provide a method, which allows correction of measured values of a sensor element that is connected in a cyclically alternating manner, and is achieved, according to example embodiments of the present invention, by correcting the individual measured values as a function of the respective switching position. Since the switching-over between the different circuit states is carried out periodically, the influence on the measurement is also periodic and, consequently, systematic and deterministic in a certain manner. Using the switching position within the measuring period, the operating state of the sensor element preceding the individual measurement, and therefore, the influence of the preceding circuit configuration on the individual measured value, is known. Accordingly, the individual measured values may be corrected as a function of the switching position within the measuring period. While the low-pass filters used by the related art to correct the measured values over all of the switching positions may produce a dynamic loss, this does not occur in the method of the present invention. By correcting the individual measured values, the measured value determined from the individual measured values is also corrected.

According to a particularly preferred example embodiment of the present invention, it may be provided that in a first phase, an approximate value for the measured value be ascertained; in a learning phase, the deviations of the individual measured values from the approximate value be determined as a function of the respective switching positions within the measuring period; correction values for correcting the individual measured values be determined for the different switching positions; and in an application phase, the individual measured values be corrected, using the correction value assigned to the respective switching position. Thus, the correction values for the individual measured values are learned in the learning phase as a function of the switching position and may be stored, for example, in a nonvolatile data memory, so that when the internal combustion engine is restarted, they are already available for correction. The actual correction of the individual measured values, using the correction values learned for the respective switching positions, then takes place in the application phase.

A precondition for the ascertainment of the correction values dependent on the switching position is that the approximate value of the measured value is known for the determination of the deviations of the individual measured values from this approximate value. Therefore, it may be provided that in the first phase, the approximate value be calculated as an average value over the individual measured values during a measuring period or over a plurality of measuring periods.

The accuracy of the correction of the individual measured values, and therefore, of the measured value, may be improved by calculating the correction values, which are used in the application phase for the respective switching positions, as average values or as moving averages of the correction values determined for the respective switching positions in a plurality of measuring periods. In this connection, the calculation of the average or the calculation of the moving average may be carried out individually for each correction value in the form of low-pass filtering.

If it is provided that the first phase, the learning phase, and the application phase run simultaneously, then the correction values may be adapted constantly. Correction values continually updated in this manner are used for correcting the individual measured values.

A marked improvement in the correction of the pump current of a wide-range lambda probe may be achieved by correcting the pump current of a wide-range lambda probe as a function of operating parameters of an internal combustion engine and subsequently correcting the individual measured values of the pump current.

Taking into account the pressure dependence, and therefore the rotational-speed dependence, of the pump current of a wide-range lambda probe results in marked smoothing of the measuring signal. Therefore, the rotational speed of the internal combustion engine may be used as its operating parameter.

The pump current for the pump cell of a wide-range lambda probe is set so that the Nernst voltage occurring at an unenergized, corresponding Nernst cell assumes a value of 450 mV. In order that this method may be considered as a measure of the combustion air ratio lambda, an air reference is generated by unipolar current pulses at the Nernst cell. However, these unipolar current pulses may generate an unwanted polarization of the Nernst cell, which influences the Nernst voltage of the unenergized Nernst cell. The approximate value for the pump current lies particularly close to the correct value, when, in the first phase, during the determination of the approximate value, the average value over individual measured values is calculated during switching positions, in the case of which no polarization of the Nernst cell is to be expected in the preceding switching position.

The method may be preferably used, in order to correct the pump current of a wide-range lambda probe for determining the combustion air ratio lambda in the exhaust gas of internal combustion engines.

The present invention is explained in greater detail below, with reference to an example embodiment shown in the figures.

DETAILED DESCRIPTION

Figure 1:
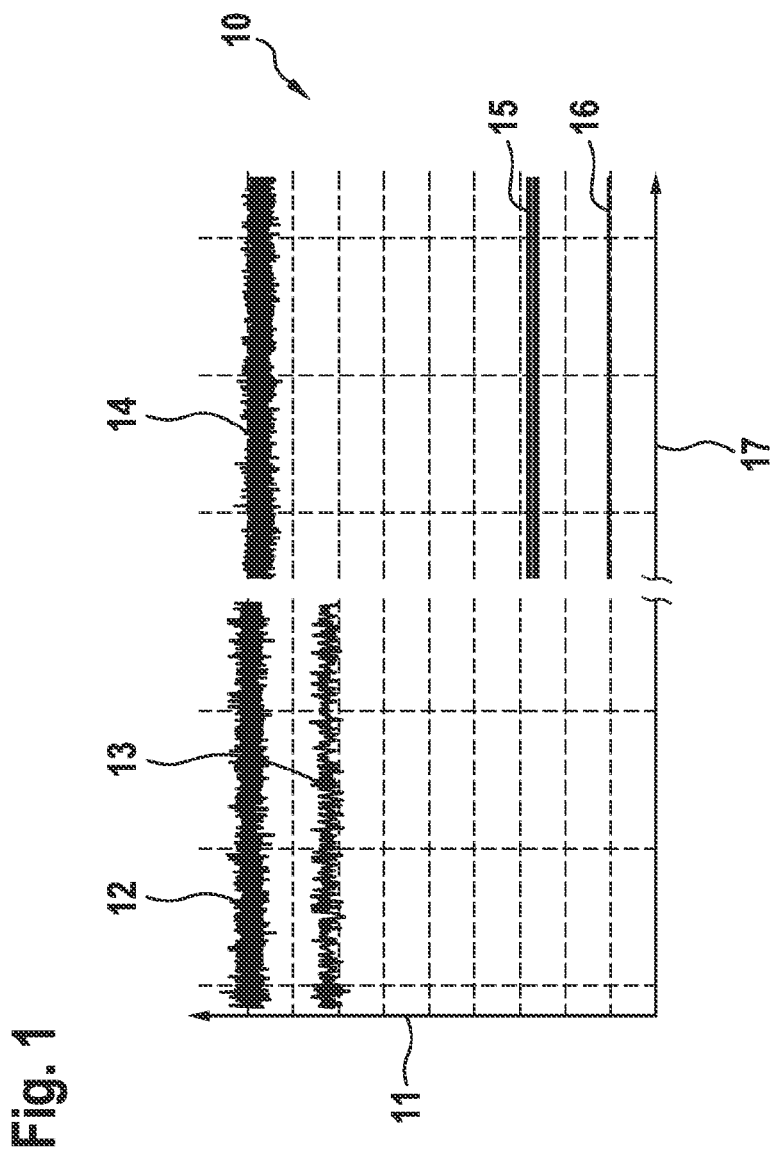
FIG. 1 is a time-dependency diagram of a pump current of a wide-range lambda probe; and, FIG. 2 is a time-dependency diagram of the pump current in a dynamic operational case.

FIG. 1 shows a first pump current diagram 10 with a first signal axis 11 and a first time axis 17. Signals from an electric measuring system for operating a wide-range lambda probe including a pump cell and a Nernst cell are represented in first pump current diagram 10. An ASIC of the type CJ135, which assumes 15 different circuit states within a measuring period of 9.99 milliseconds in order to carry out measuring and diagnostic functions, is used in the electric measuring system. If the measuring system is operated without the correction function of the present invention, a group of first pump current values 12 and a group of second pump current values 13 is produced during a measuring cycle. A reason for differences occurring between first pump current values 12 and second pump current values 13 is the polarization of the Nernst cell of the wide-range lambda probe occurring in some circuit states of the ASIC CJ135.

According to the present invention, an approximate value for the pump current is calculated from first pump current values 12 and second pump current values 13. Correction values, which are plotted in first pump current diagram 10 as first correction values 15 and second correction values 16, are calculated from the deviations of first pump current values 12 and second pump current values 13 from the approximate value. Thus, a total of 15 correction values are calculated, one correction value for each circuit state of the ASIC CJ135. In this context, a moving average, which is stored in a nonvolatile data memory, is calculated by a low-pass filter for each individual correction value, over several measuring periods. First pump current values 12 and second pump current values 13 are corrected, in each instance, using the corresponding values from first correction values 15 and second correction values 16, and corrected pump current values 14 are calculated.

Figure 2:
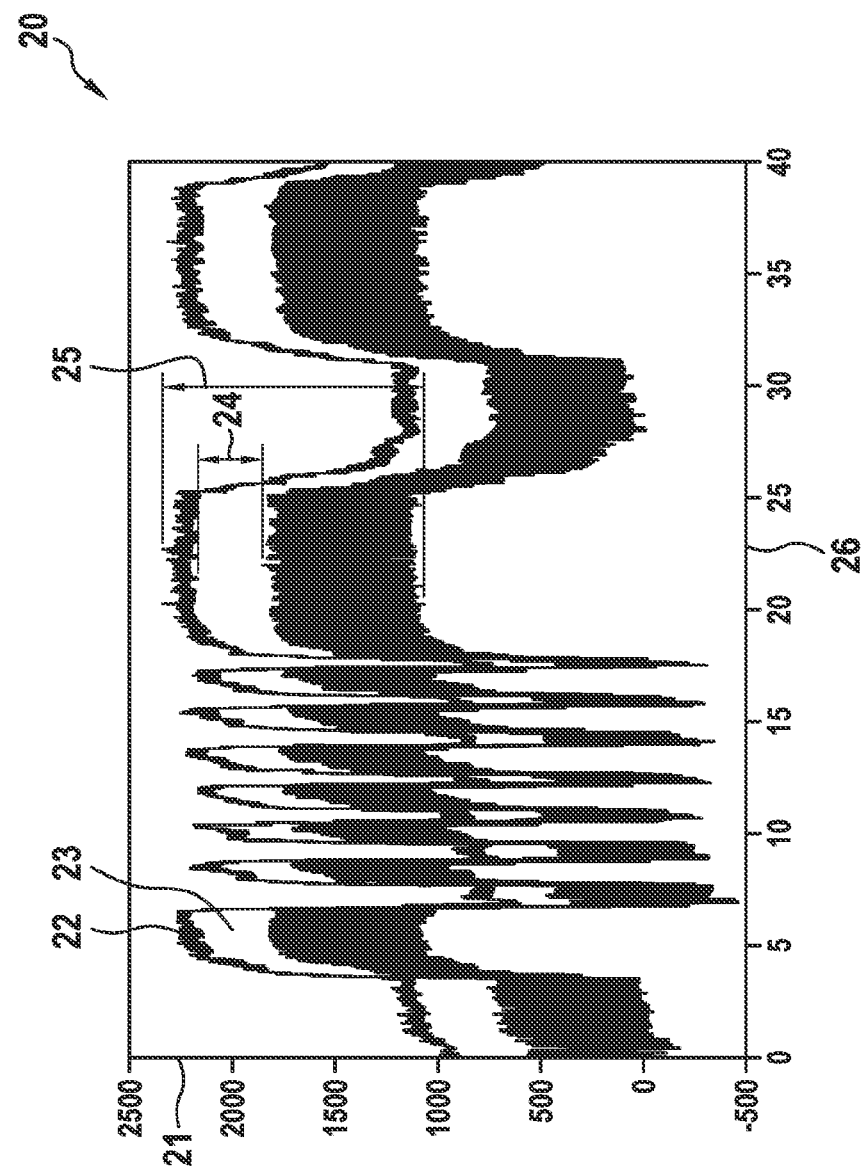

In a second pump current diagram 20, FIG. 2 shows a signal characteristic for a dynamic operational case of an internal combustion engine. On a second signal axis 21, a first pump current characteristic 22 (the values of which are depicted in black) without correction and a second pump current characteristic 23 (depicted in white superimposed over current characteristic 22) with the correction of the present invention are depicted along a second time axis 26. In this context, in a middle region of second time axis 26, first pump current characteristic 22 sweeps over a first pump current range 25, which extends from the lowest values shown in black to the highest values shown in black. In second pump current diagram 20, use of the correction of the present invention limits first pump current range 25 to a second pump current range 24. It is apparent that the method of the present invention improves the accuracy in the determination of the required pump current. According to an example embodiment, a further improvement in the method is achieved by taking into account that pressure differences in the exhaust duct of the internal combustion engine influence the pump current. These may be taken into account by correcting the pump current values as a function of the rotational speed of the internal combustion engine.

What is claimed is:

1. A method for correcting individual measured values of a sensor element obtained over repeatedly executed measuring periods for performing different measurements and for setting different operating states, the sensor element is electrically connected by a circuit arrangement in a periodically alternating electrical manner, in consecutive switching positions, in a predefined order, the method comprising:
performing a measurement repeatedly within a measuring period, at predefined switching positions, the individual values thereby being determined at the predefined switching positions; and
correcting, by processing circuitry, the individual values as a function of the respective switching positions associated with respective ones of the individual values.

2. The method of claim 1, wherein the correcting includes:
in a first phase, ascertaining an approximate value for the measured value;
in a learning phase:
   determining deviations of the individual values from the approximate value and correlating the deviations to the respective switching positions associated with the respective individual values for which the respective deviations are determined; and
   determining respective correction values for correcting the individual values for respective ones of the different switching positions; and
in an application phase, correcting the individual values using the respective correction values assigned to the respective switching positions of the respective individual values to be corrected.

3. The method of claim 2, wherein, in the first phase, the approximate value is calculated as an average value of the individual values determined during one or more measuring periods.

4. The method of claim 2, wherein the correction values used in the application phase for the respective switching positions are calculated as average values or as moving averages of the correction values determined for the respective switching positions in a plurality of measuring periods.

5. The method of claim 2, wherein the first phase, the learning phase, and the application phase are executed simultaneously.

6. The method of claim 2, wherein:
   the sensor element is a wide-range lambda probe that includes a pump cell and a Nernst cell;
   the measured value is a pump current for the pump cell of the wide-range lambda probe; and
   in the first phase, the approximate value is calculated as an average value of the individual values calculated for switching positions where no polarization of the Nernst cell is to be expected in a preceding switching position.

7. A method for determining a combustion air ratio lambda in exhaust gas of an internal combustion engine, the method comprising:
   obtaining a measured value of a pump current of a wide-range lambda probe; and
   determining the combustion air ratio lambda based on the measured value;
wherein:
   the wide-range lambda probe is electrically connected by a circuit arrangement in a periodically alternating electrical manner, in consecutive switching positions, in a predefined order; and
   the obtaining of the measured value includes, during repeatedly executed measuring periods for performing different measurements and for setting different operating state, performing the following:
      performing a pump current measurement repeatedly within a measuring period, at predefined switching positions, individual values thereby being determined at the predefined switching positions; and
      correcting, by processing circuitry, the individual values as a function of the respective switching positions associated with respective ones of the individual values.

* * * * *